United States Patent [19]

Leuenberger

[11] Patent Number: 5,849,933
[45] Date of Patent: Dec. 15, 1998

[54] PROCESS FOR PRODUCING ASCORBIC ACID-2-MONOPHOSPHATES

[75] Inventor: Bruno Leuenberger, Basel, Switzerland

[73] Assignee: Roche Vitamins Inc., Parsippany, N.J.

[21] Appl. No.: 733,897

[22] Filed: Oct. 18, 1996

Related U.S. Application Data

[63] Continuation of Ser. No. 857,351, Mar. 25, 1992, abandoned.

[30] Foreign Application Priority Data

Apr. 10, 1991 [CH] Switzerland .............. 1072/91

[51] Int. Cl.⁶ .................................................. C07F 9/06
[52] U.S. Cl. ..................................................... 549/222
[58] Field of Search ............................................. 549/222

[56] References Cited

U.S. PATENT DOCUMENTS

| | | |
|---|---|---|
| 4,647,672 | 3/1987 | Seib . |
| 5,110,951 | 5/1992 | Ishimura et al. .................. 549/222 |

FOREIGN PATENT DOCUMENTS

| | | |
|---|---|---|
| 0 229 154 | 6/1986 | European Pat. Off. . |
| 8700172 | 1/1987 | WIPO ................................. 549/222 |
| WO 87/00172 | 1/1987 | WIPO . |

*Primary Examiner*—Johann Richter
*Assistant Examiner*—Joseph Murray
*Attorney, Agent, or Firm*—George W. Johnston; Dennis P. Tramaloni; Bruce A. Pokras

[57] ABSTRACT

The process for manufacturing ascorbic acid 2-monophosphates from ascorbic acid 2-polyphosphates, in particular 2-triphosphates by subjecting the ascorbic acid 2-triphosphates to drying conditions.

6 Claims, No Drawings

PROCESS FOR PRODUCING ASCORBIC ACID-2-MONOPHOSPHATES

This is a continuation of application Ser. No. 07/857,351, filed Mar. 25, 1992 now abandoned.

SUMMARY OF THE INVENTION

The invention is concerned with a process for the manufacture of ascorbic acid 2-monophosphates (AAMP) from ascorbic acid polyphosphates, in particular 2-triphosphates (AATP) by subjecting AATP to drying conditions.

DETAILED DESCRIPTION OF THE INVENTION

In accordance with this invention, it has been discovered that when ascorbic acid polyphosphates, in particular 2-triphosphates are subjected to drying conditions, the ascorbic acid 2-triphosphates are converted to ascorbic acid 2-monophosphates.

In accordance with this invention, any conventional drying conditions can be utilized for converting the polyphosphates, e.g. the triphosphates to the 2-monophosphates. The polyphosphates, e.g. the 2-triphosphates to be converted can be in any form such as a powder, or dissolved in a solvent such as water. Preferably, the preferred form of AATP for conversion to AAMP is in an aqueous solution. While any convention drying conditions can be utilized to carry out the conversion of this invention, drying is conveniently carried out by spray drying, spin drying, fluidized bed drying or belt drying using conventional apparatuses which will be known to a person skilled in the art. Spray drying is the preferred drying condition.

For completeness sake, it should be mentioned that the conversion of the AATP to AAMP, very probably, passes through the intermediate ascorbic acid 2-diphosphate.

The suitable temperatures are about 110° C. to about 200° C.

The suitable parameters will be evident from the following compilation.

Spray drying[2]
   Air inlet: about 200°–160° C. esp. about 180° C.
   Air exit: about 150°–110° C. esp. about 120° C.
Spin drying about 120°–160° C.
Belt drying about 120°–160° C.

[2] Analogous values apply to fluidized bed drying.

The starting material is conveniently used as an aqueous solution, conveniently in a pH range of about 4 to about 7, especially of about 5.5 to about 6.5.

In accordance with this invention, any basic salt of the polyphosphates can be utilized in this conversion. The choice of the cation which forms such salts are not critical. However, alkali metal and alkaline earth metal cations, especially sodium and calcium, are of primary interest.

The aqueous solution conveniently has a solid content of about 10–80 wt. %, especially of about 40–60 wt. %. Such solutions can be obtained, for example, in accordance with EP-PS 229154 of 27.12.1990, namely from ascorbic acid by reaction with a soluble salt of metaphosphoric acid.

In accordance with EP-PS 229154 it is possible to produce AAMP by the acidic hydrolysis of AATP. It is surprising that now by simple drying the almost complete conversion of AATP into AAMP can be achieved and in this manner a commercial product which is stable upon storage results. The AATP content of this product of is always $\leq 10\%$. It is, however, also possible to come to about 1 wt. %.

EXAMPLE

An aqueous solution of AATP (see below) is produced in accordance with EP-PS 229154, Example 1, starting from 55 kg of AA (see below). The solution is brought to a pH value of 6.5–5.5 and then spray-dried using a Niro dryer (Niro Atomizer, DK 2860 Söborg) with an air inlet temperature of 180° C. and an air exit temperature of 120° C. The analysis gives the following picture:

| AAxP:      | AA   | AAMP | AADP | AATP  |
|------------|------|------|------|-------|
| Before SD: | 0.6% | 0.0% | 0.7% | 11.0% |
| After SD:  | 1.2% | 7.3% | 2.4% | 1.0%  |

AAxP: Ascorbic acid phosphate (type)
AA: Ascorbic acid
AAMP: Ascorbic acid monophosphate
AADP: Ascorbic acid diphosphate
AATP: Ascorbic acid triphosphate
%: The details are expressed as AA equivalents, i.e. as the weight percent of ascorbic acid equivalents based on the dry substance; e.g. 11% AATP means that the corresponding product, based on the solid content, contains 11% ascorbic acid in the form of ascorbic acid triphosphate.
SD: Spray drying SD: Spray drying

I claim:

1. A process for producing ascorbic acid 2-monophosphates from ascorbic acid 2-triphosphates comprising subjecting said triphosphates in an aqueous solution at a pH of from 4 to about 7 to drying conditions at about 110° C. to about 200° C. whereby said monophosphates are formed.

2. The process of claim 1, wherein the aqueous solution is subjected to spray drying, spin drying, belt drying or fluidized bed drying.

3. A process of claim 1, wherein the salt is an alkali metal or an alkaline earth metal salt.

4. The process of claim 1, wherein the aqueous solution has a pH of from about 5.5 to about 6.5.

5. The process of claim 1, wherein the aqueous solution contains from about 10 to about 80 wt. % of the triphosphate or salt thereof.

6. The process of claim 5 wherein the aqueous solution contains from about 40 to about 60 wt. % of the triphosphate or salt thereof.

* * * * *